(12) United States Patent
Schleifenbaum et al.

(10) Patent No.: US 7,226,613 B2
(45) Date of Patent: Jun. 5, 2007

(54) SEAMLESS FILLED CAPSULES

(75) Inventors: Birgit Schleifenbaum, Caligny (CH); Ines Voigt, Hamburg (DE); Frank Aickele, Holzminden (DE)

(73) Assignee: Symrise GmbH & Co. KG (DE)

( * ) Notice: Subject to any disclaimer, the term of this patent is extended or adjusted under 35 U.S.C. 154(b) by 652 days.

(21) Appl. No.: 10/728,653

(22) Filed: Dec. 5, 2003

(65) Prior Publication Data
US 2005/0079215 A1   Apr. 14, 2005

(30) Foreign Application Priority Data
Dec. 5, 2002 (EP) .................. 02027190

(51) Int. Cl.
  *A61K 9/64* (2006.01)
  *A61K 9/68* (2006.01)
(52) U.S. Cl. .................. 424/456; 424/440
(58) Field of Classification Search ......... 424/456, 424/464, 492, 489, 488, 486, 471, 496, 440
See application file for complete search history.

(56) References Cited

U.S. PATENT DOCUMENTS

| 4,251,195 A | 2/1981 | Suzuki |
| 4,481,157 A | 11/1984 | Morishita |
| 4,517,216 A | 5/1985 | Shim |
| 4,935,243 A | 6/1990 | Borkan et al. |
| 5,300,305 A | 4/1994 | Stapler |
| 5,370,864 A * | 12/1994 | Peterson et al. ............. 424/49 |
| 5,620,707 A | 4/1997 | Sanker |
| 5,780,056 A * | 7/1998 | Akamatsu et al. .......... 424/464 |
| 5,939,097 A | 8/1999 | Fusejima |
| 6,258,380 B1 | 7/2001 | Overholt |
| 2001/0024678 A1 * | 9/2001 | Scott et al. ............... 426/656 |

FOREIGN PATENT DOCUMENTS

| JP | 63170310 | 7/1988 |
| JP | 1037259 | 2/1989 |
| JP | 4027352 | 1/1992 |
| WO | WO 96/29986 | 10/1996 |
| WO | WO 00/51574 * | 9/2000 |
| WO | WO 2004/050069 A1 * | 6/2004 |

* cited by examiner

*Primary Examiner*—Sharon Kennedy
(74) *Attorney, Agent, or Firm*—Akerman Senterfitt

(57) ABSTRACT

Spherical capsule having a liquid core and a seamless solid shell surrounding the core, in which: the diameter of the capsule is in the range of 4-8 mm; the thickness of the shell is in the range of 20-200 μm; the shell thickness to capsule diameter ratio is in the range of 0.004-0.04; the shell contains 70-90% (m/m) gelatin and 10-30% (m/m) plasticizer, based on the solids content of the shell; and the core has a flavoring content in the range of 1-100% (m/m), based on the total mass of the core.

22 Claims, No Drawings

SEAMLESS FILLED CAPSULES

FIELD OF THE INVENTION

The present invention relates to spherical capsules having a liquid core and a seamless, solid shell surrounding this core; the core of these capsules comprises a flavoring component and the shell comprises gelatin. The invention also relates to methods for the preparation of such capsules and to curable shell mixtures (shell formulations) for use in the preparation of the capsules according to the invention. The capsules according to the invention are characterized in that they are suitable for immediate consumption without further processing and can be sucked or chewed in the mouth without the shell being found to be annoying.

BACKGROUND OF THE INVENTION

Flavorings are used in foods in order to achieve taste impressions. In the sense of the present invention a flavoring is to be understood to be a single substance (flavoring) or a mixture of substances (flavorings) which have the organoleptic property or properties. These organoleptic properties include the characteristic of imparting a specific odor or taste to a mixture and the characteristic of giving rise to specific stimuli, which are transmitted via the trigeminus nerve and are thus detected.

Oils, such as, for example, vegetable oils and other triglycerides, which are used as solvents for the flavoring and themselves have a neutral odor and taste are not regarded as flavorings below.

If flavorings are to be ingested by a consumer in portions in the form of a liquid, the use of a capsule in which a core of a quantity of liquid containing flavoring is surrounded by a solid shell is an obvious measure. In this context the following problems and requirements, in particular, must be taken into consideration:

1. For optimum organoleptic detection, the release of the liquid core containing flavoring must already take place in the mouth. Appropriately it should be possible to consume the capsule including the shell, since separation of shell and liquid core is problematical after the capsule has been placed in the mouth.
2. Achieving a pleasant feeling in the mouth when consuming gelatin capsules is a technological challenge. In particular, hitherto it has been found to be disadvantageous that the majority of shells of ready-to-consume capsules available commercially are detectable as an unpleasant, rubbery, tough residue. Corresponding observations are made and found to be particularly negative especially in the case of large filled capsules (diameter θ 4 mm).
3. On consumption, a capsule shell in the mouth should preferably (a) not have a disturbing haptic effect (b) be easy to bite and (c) dissolve rapidly. The core liquid containing flavoring that is to be released or is released should give rise to a sensory effect with a substantial impact in the mouth.
4. At the same time, the capsule should be easy to handle, that is to say have a certain minimum size; in the case of spherical capsules in many cases a diameter θ of 4 mm is preferred.
5. In addition, for ease of handling during transport, storage and use the capsule should have an adequate temperature stability. In this context it is desirable that the capsules do not stick together even at temperatures above 30° C.

Spherical capsules having a liquid core and a solid shell surrounding this core are known and capsules having a diameter of more than 4 mm can, for example, be prepared by the rotary die method or, in the case of the capsules having a seamless shell, which are of particular interest, by a drip method using a multi-component nozzle (cf. Bauer, Frömming, Führer; Pharmazeutische Technologie; 1997). This method is also designated a multi-component nozzle method below. In this context (insofar as nothing different results from the context) references to the multi-component nozzle method are also to be understood as references to a multiplicity of related methods for the preparation of seamless capsules.

In the rotary die method capsules having a seam in the shell are produced via a punching method using rotary shaping rollers, in which method the capsule wall is made up and shaped from two gelatin halves that have been punched from a gelatin strip. For the preparation of soft gelatin capsules by the rotary die method stringent requirements are imposed in respect of the air conditioning. 20-30% relative atmospheric humidity at approximately 22° C. must be guaranteed in all production and packing areas.

In the multi-component nozzle method capsules having a seamless shell are prepared by a drip method. With this method a lipophilic core material and a hot gelatin solution are usually simultaneously pumped through a concentric multi-component nozzle so that they drip into a cold lipophilic cooling liquid, for example vegetable oil. With this method the nozzle can dip directly into the cooling liquid. When they drip in the capsules assume a ball shape (spherical shape) as a result of the surface tensions. As a result of the fall in temperature on contact with the cooling liquid, the gelatin-containing seamless capsule shell solidifies.

U.S. Pat. No. 4,481,157 and U.S. Pat. No. 4,251,195 describe methods and equipment for the continuous preparation of seamless capsules by the multi-component nozzle method where the nozzle dips into the cooling liquid.

JP 52-148635 describes a capsule having a diameter of 0.5-4 mm for immediate consumption. The wall thickness of the capsule is 50 μm-200 μm. A capsule diameter of more than 4 mm is not described.

However, a capsule diameter of 4 mm and more is required for better handling and portioning in the case of direct consumption and a strong flavoring impact by a single capsule in the mouth.

However, the larger a capsule the more difficult it is to achieve a thin, stable shell, since the stability of the capsule decreases substantially on drying and during transport as the capsule diameter/shell thickness ratio increases. Moreover, the centring of the core and the uniform enclosure of the core by a shell is extremely problematical in the case of large capsules.

U.S. Pat. No. 5,939,097 describes a food that contains capsules, which, in turn, contain a pharmaceutical active substance, the ratio of shell thickness to capsule diameter being 0.01-0.05 for capsule diameters of 0.5-5 mm. The capsules are intended to be incorporated in the food and are to be swallowed whole with the latter. The capsule is intended to release the core only in the gastrointestinal tract. The capsule shell contains gelatin or agar. No further details of the composition of the shell are given. Plasticizers are not mentioned.

U.S. Pat. No. 5,300,305 describes seamless capsules having a diameter of 2-9 mm, which are suitable for immediate consumption and are used to control bad breath. With these capsules, active substances for bad breath control are incorporated in the shell of the capsules on solubility grounds. The capsules are intended to remain in the mouth for a prolonged period so that the active substance influencing the bad breath is able to dissolve from the shell and give rise to a long-lasting effect in the mouth. The shell thickness is in the range of 30 µm to 2 mm. Illustrative embodiments show shell contents of not less than 13% (m/m) and only low plasticizer contents (sorbitol <10%, based on the shell). The capsule contains up to 25% (m/m) flavoring in the core, based on the total mass of the capsule. The capsules are, for example, prepared by a multi-component nozzle process.

The capsule shell was developed with a view to slow dissolution in the mouth and the Applicant's experiments have now shown that it proves to be rather hard and annoying when sucked. Accordingly, in particular the adverse sensation in the mouth, that is caused by the shell residues dissolving only slowly in the mouth, is a disadvantage when using the capsule described in U.S. Pat. No. 5,300,305 for an immediate, strong flavoring impression. Moreover, as has been mentioned, the flavoring content in the capsule is restricted to 25% and it is therefore not possible to achieve a strong flavoring impact.

U.S. Pat. No. 4,935,243 describes a soft gelatin capsule, the shell of which decomposes rapidly on chewing. The shell consists of water (15-30%), plasticizer (17.5-35%) and a small proportion of hydrated hydrolyzed starch (5-25%). Illustrative embodiments show shell solutions which have a solids content of approximately 75%.

A disadvantage is found to be in particular that, because of the high solids content and the resulting high viscosity, the shell formulations of U.S. Pat. No. 4,935,243 are suitable only for a rotary die method and not for a drip method, that is to say for the preparation of capsules with a seam, but not for the preparation of seamless capsules by, for example, the multi-component nozzle method.

WO 96/29986 describes seamless capsules having a diameter of 2-9 mm, which contain a pharmaceutical active substance against coughing. The capsule shells are 30 µm-500 µm thick and are intended to dissolve within 3.5-5 minutes. The capsule shells contain at least 10% water. A shell thickness to capsule diameter ratio is not given.

A disadvantage of the capsules according to WO 96/29986 is, in particular, the indicated slow rate of dissolution of the shell.

U.S. Pat. No. 5,620,707 describes seamless spherical capsules having a diameter of 2-15 mm and a shell thickness of 30 µm-2000 µm for use in drinks which contain flavoring, acesulfame and a further sweetener in specific proportions in the core. It can be seen from the illustrative embodiments that the shell contains more than 10% water and that sorbitol in amounts of more than 15% is used as plasticizer in the shell. A formulation with no plasticizer at all is also mentioned.

SUMMARY OF THE INVENTION

A primary aim of the present invention was to indicate spherical capsules of the initially mentioned type that are suitable for immediate consumption without further processing and can be sucked or chewed in the mouth without the shell being found to be annoying. At least some, but preferably all, the problems and requirements indicated above were to be solved or taken into account. In addition, a method of preparation for the capsules that is practicable on an industrial scale was to be indicated. Moreover, it was to be possible to dispense with drying in the presence of separating agents, which usually is associated with an adverse turbidity of the capsule shell.

A particular (subsidiary) aim of the present invention was to indicate a spherical seamless capsule having a shell only 20-200 µm thick, a diameter in the range of 4-8 mm and a shell thickness to capsule diameter ratio in the range of 0.004-0.04, the shell of which, which is still moist during the preparation prior to drying, still remains dimensionally stable even at temperatures of 40° C. -60° C. By this means both a higher drying rate (as a result of the possible use of higher drying temperatures) and also improved storability and transportability were to be achieved.

According to the invention, to achieve the stated aim(s) a spherical capsule having a liquid core and a seamless solid shell surrounding this core is indicated, wherein the diameter of the capsule is in the range of 4-8 mm, the thickness of the shell is in the range of 20-200 µm, the shell thickness to capsule diameter ratio is in the range of 0.004-0.04, the shell contains 70-90% (m/m) gelatin and 10-30% (m/m) plasticizer, based on the solids content of the shell, and the core has a flavoring content in the range of 1-100% (m/m), based on the total mass of the core. The capsule can be prepared by a multi-component nozzle method; it is suitable for direct consumption without further processing and can be sucked or chewed in the mouth without the shell being found to be annoying. If a suitable drying method (without separating agent) is chosen, the capsule shell is glossy and transparent. In this context a capsule is designated a spherical capsule insofar as the ratio between the largest and the smallest diameter of the capsule is not more than 1.2. This arithmetic mean of the largest and the smallest diameter of the capsule is designated as the diameter of a capsule according to the invention below.

For the organoleptic assessment it is particularly advantageous if the diameter of the capsule is in the range of 4.5-6.5 mm, the thickness of the shell is in the range of 50-150 µm and the ratio of shell thickness to capsule diameter is in the range of 0.01-0.03. It is most advantageous if the diameter of the capsule is in the range of 4.5-5.5 mm, the thickness of the shell is in the range of 50-90 µm and the ratio of shell thickness to capsule diameter is in the range of 0.01-0.02.

Preferred embodiments of the capsule according to the invention result from the following description, the examples and the patent claims.

DETAILED DESCRIPTION

Shell Thickness:

For rapid dissolution of the shell of a capsule according to the invention in the mouth the shell thickness should be as small as possible. For a constant core/shell mass ratio the shell thickness increases substantially with increasing capsule diameter.

The capsules according to the invention have a shell thickness of only 20 µm-200 µm despite the large capsule diameter of 4-8 mm. In these capsules the ratio of shell thickness to capsule diameter is in the range of 0.004-0.04. These data relate to the dried capsule. The capsule diameter can be determined using a micrometer screw. For determination of the shell thickness a cross-section of the capsule is prepared. The thickness of the shell can be determined via a microscope with image processing. To this end the thickness of the capsule shell is measured at various points in the latter and the mathematical mean for the shell thickness is determined.

With the composition of the shell selected in accordance with the invention (in this context see below) high process and transport stability, adequate elasticity, good biteability and a sufficiently high dissolving power in the mouth are ensured.

Composition of the Shell:

Viscosity of the Shell Mixture/Gel Point:

When shaping a capsule according to the invention by means of a multi-component nozzle method particular attention has to be paid to the viscosity and the gelling characteristics of the curable shell mixture. Too low a viscosity or too low a gel point prevent a capsule shell that is sufficiently solid in the wet state. Corresponding capsules would be mechanically destroyed by the further processing steps, such as, for example, centrifuging. Too high a viscosity and too high a gel point, on the other hand, prevent correct capsule shaping and, moreover, give rise to undesired, substantial satellite formation.

The viscosity of preferred shell mixtures for the preparation of capsules according to the invention was determined using a CVO 120 rheometer (Bohlin Instruments GmbH, Pforzheim). The measurement system used was a plate-plate system with a plate diameter of 50 mm. The measurements were carried out using rotation. The shear rate was 50 $s^{-1}$; the gap was set at 500 μm. The measurements were carried out isothermally; the temperature was 80° C.

At 80° C. preferred shell mixtures have a viscosity in the range of 30 mPas to 300 mPas, preferably of 40 mPas to 150 mPas, and particularly preferentially of 50 mPas to 90 mPas.

The gel point of preferred shell mixtures for the preparation of capsules according to the invention was likewise determined using a CVO 120 rheometer (Bohlin Instruments GmbH, Pforzheim). The measurement system used was a plate-plate system with a plate diameter of 50 mm. The measurements were carried out using oscillation. The frequency was constant at 1 Hz, the gap was set at 500 μm and the temperature was lowered from 80° C. to 10° C. with a gradient of 5° C./min. The temperature at which the viscosity or memory module G' is equal to the modulus of elasticity or loss module G" was read off as the gel point, the sol/gel transition point (Thomas Mezger, Das Rheologie Handbuch, 2000).

The gel points of preferred shell mixtures according to the invention are between 15° C. and 60° C., preferably between 20° C. and 40° C. and particularly preferentially between 25° C. and 35° C.

Gelatin:

The shell of the capsules according to the invention contains gelatin and plasticizer. The grade and amount of the gelatin and of the plasticizer have an effect on the solubility kinetics of the shell in the mouth.

For capsule shaping, aqueous solutions containing 10-40% (m/m), preferably 15-30% (m/m) and particularly preferentially 18-25% (m/m) gelatin are preferably used for the shell.

The gelatin used in the capsules according to the invention is in many cases obtained by partial hydrolysis of collagen-containing material from animals, such as, for example, pigs, cattle, fish or poultry. Type A gelatin is obtained by acid digestion, usually of pig or fish skins, whilst type B gelatin is obtained by alkaline digestion, usually of cattle bones and skins.

The term Bloom is used to characterize the gel strength of gelatin. In the determination of the Bloom value a stamp of a Bloom gelometer or texture analyser 12.7 mm (0.5 inch) in diameter is pressed 4 mm deep into a 6.67% gelatin gel that has been aged for 18 hours at 10° C. prior to the measurement. The result is given in "Bloom", corresponding to the weight in grams that is loaded onto the stamp in order to achieve the impression depth (see Schormüller, Handbuch der Lebensmittelchemie, Volume III, 1968 and British Standard Method for Sampling and Testing Gelatin (BS757; 1975)).

A gelatin having a Bloom value of more than 200, particularly preferentially having a Bloom value of 240-300, and specifically preferably a Type A gelatin is preferably used for the preparation of capsules according to the invention. By this means adequate stability of the shell is made possible during the preparation of the capsule and during transport, despite the small thickness of the capsule shell.

Gelatin grades that have been obtained from cattle, poultry or fish are also suitable for the preparation of the capsule according to the invention. In this context, in any event, as already mentioned, care must be taken that the viscosity and the gelling characteristics are correctly adjusted. Fish gelatins that can be used are both grades from cold water fish and grades from warm water fish. Mixtures of different gelatin grades can also be used. Details can be taken from the examples.

Achieving high process stability of a capsule coupled with rapid solubility of the capsule shell in the mouth is a particular technical problem. On the one hand, it is advantageous, specifically for the process for preparation of the capsule and for storage, to select a shell formulation that gives the capsule a particularly high mechanical strength and rapidly forms a solid gel that after drying is as hard as possible and absorbs little water. On the other hand, for a good sensation in the mouth on consumption of the capsule it is advantageous if the shell absorbs water rapidly, is soft and flexible and dissolves quickly.

Surprisingly, it has been found that this particular technical problem can be solved by the use of a mixture of a hydrolyzed gelatin with a Bloom value of 0 and a high-Bloom gelatin with a Bloom value of 200 and above (preferably a Bloom value in the range of 240-300). Presumably the high-Bloom gelatin forms a solid network here that is important for the process stability. The hydrolyzed 0-Bloom gelatin presumably occupies spaces in this network and in the mouth leads to a more rapid absorption of water and thus solubility of the entire shell. See Example (sic) 25 and 27 below.

Hydrolyzed 0-Bloom gelatin has no gelling power and is readily soluble in water at 20° C. In this 0-Bloom gelatin the polypeptide chains have been very substantially decomposed by acid or enzymatic hydrolysis. To date it is therefore also not used for the formation of capsule shells but is used only, for example, as a nutrient (protein source), as an emulsifier or also for clarifying wine.

Shell mixtures consisting of (a) hydrolyzed 0-Bloom gelatin, that has been obtained from any desired species of animal, with (b) gelatin that has a Bloom value of $\geq 200$ are preferably suitable for solving the particular technical problem, the proportion of hydrolyzed 0-Bloom gelatin preferably being in the range of 0.5-90% (m/m), based on the solids content of the shell.

Here the gel point of the high-Bloom gelatin constituent is the decisive factor determining the gel point of the mixtures (see the appended table "Gel points").

The flexibility of a film produced from a shell mixture is, moreover, surprisingly high if the mixture contains 0-Bloom gelatin (see the appended table "Gel point" (sic)).

A further possibility for solving the abovementioned particular technical problem consists in the mixture of certain low-Bloom (Bloom value <200) fish gelatins with high-Bloom gelatin (Bloom value ≧200).

The lower the Bloom value of a gelatin, the lower are, in general, the gel point, the viscosity and the mechanical stability of the moist solidified gel. Mixtures of gelatin having a low Bloom value and a medium Bloom value in order to achieve an improved solubility of the capsule shell in the mouth are known. U.S. Pat. No. 6,258,380 describes shells of this type. However, in this patent no specification of the gelatins has been given beyond the Bloom value.

Surprisingly, it has now been found that when fish gelatin is used as the gelatin fraction having a low Bloom value (<200) and at the same time a high-Bloom gelatin having a Bloom value of 200 and above is used, a further improved solubility in the mouth can be achieved. This is presumably affected by the lower gel point of fish gelatins (below 28° C.) compared with pig, cattle and poultry gelatins (approximately 28-40° C.).

Fish gelatin grades with a gel point of <20° C. and grades that are prepared from cold water fish, for example cod, are particularly suitable since their gel points at approximately 10-20° C. are even below those of gelatins from warm water fish (gel point approximately 20-28° C.), such as, for example, from carp. In this context the cold water fish include all species of fish that live predominately in waters at temperatures of 18° C. and below. Research by Choi and Regenstein (Journal of Food Science Vol. 65, No. 2, 2000) and the Applicant's research (see appended table "Gel points") confirm the lower gel points of fish gelatins compared with pig, cattle and chicken gelatins with approximately comparable Bloom values.

Presumably the protein composition is of importance for the lower gel points in fish gelatin grades. The proportions of the amino acids proline and hydroxyproline are considerably lower in the case of fish gelatins, and specifically especially in the case of cold water fish gelatins, compared with pig, cattle and poultry gelatins. Hydroxyproline and proline play an important role in the cross-linking of the protein helices with one another. Presumably folding of the helices takes place in water, water can be embedded and the solubility rises. The temperature at which this folding takes place depends on the hydroxyproline content and proline content. The lower the content, the lower the temperature at which the gelatin goes into solution.

A low gel temperature and a low solubility temperature is advantageous for good solubility in the mouth.

As a rule it is not possible to achieve adequate process stability of the capsule by using fish gelatin having a Bloom value of less than 200 as the only type of gelatin in the shell. The gel strength of the capsule shells that are still moist is frequently not adequate for further processing. The capsules are frequently mechanically too unstable.

On the other hand, the particular technical problem is solved by the admixture of such a gelatin, as readily soluble filler, to a high-Bloom gelatin that is intended to form a process-stable skeleton. In this context mixtures of fish gelatins with Bloom values of below 200 and high-Bloom pig, cattle or poultry gelatins with a Bloom value of over 200 have proved advantageous. Fish gelatin (below 200 Bloom) contents of 0.5-50% (m/m), based on the solids content of the shell, are preferred. In this context gelatin grades from cold water fish are particularly preferred.

Here it is the gel point of the high-Bloom gelatin fraction that is the decisive factor determining the gel point of the mixtures (see the appended table "gel points").

Plasticisers:

Plasticizers that can be used are, in particular, polyols, such as, for example, sorbitol, glycerol, propylene glycol, lactitol, hydrated hydrolyzed starches and trehalose. Plasticizer fractions improve the consumption characteristics of a capsule in that they reduce the hardness of the capsule shell and improve the solubility in the mouth. Moreover, plasticizers promote the flexibility of the shell and thus the stability during capsule drying and during transport.

Preferred plasticizer contents for the capsules according to the invention are not more than 30% (m/m) based on the total solids content of the shell. Higher amounts of plasticizer make drying of the capsules more difficult and also make it necessary to use packaging that excludes atmospheric humidity.

Plasticizers are preferably used in the shell in a proportion of 10-30% (m/m), particularly preferentially of 15-20% (m/m), based on the solids content of the shell. The plasticizer preferably comprises one or more polyols, preferably selected from the group which consists of glycerol, propylene glycol, sorbitol and maltitol. Glycerol is the preferred plasticizer.

Plasticizer contents of over 30% (m/m) make drying of capsules according to the invention more difficult and frequently make it necessary to use anti-caking agents, such as silica. Since, however, for optical reasons the capsules according to the invention as a rule are intended to have a transparent, glossy shell, the use of silica is not desired.

Plasticizer contents of less than 10% (m/m) allow the capsule shell of a capsule according to the invention to become increasingly brittle.

Experiments have shown that, in the case of sorbitol, contents of more than 15% (m/m) in the shell can already give rise to problems with capsule drying and would then make the undesired use of an anti-caking agent necessary.

Further (Optional) Constituents of the Capsule Shell:

Sweeteners/Colorants/Water:

In addition to gelatin and plasticizer, the shell of a capsule according to the invention can contain sweeteners, such as, for example, sucralose, aspartame, acesulfame, K or Na saccharine, thaumatin, neohesperidin, or mixtures thereof, as well as water-soluble food colorants.

The capsules are dried during the production process. During this operation a certain residual amount of water remains bound in the gelatin network. Depending on the ambient moisture content, a water content will be established in the capsule shell in equilibrium. At 20° C. and 50% relative atmospheric humidity, the equilibrium moisture content of typical capsules according to the invention is in the range of approximately 8-10% (m/m) water, based on the total mass of the capsule shell.

Hydrocolloids/Gellan Gum:

Additions of hydrocolloids to gelatin influence the solubility and thus the absorption of water as well as the temperature stability of the gels formed.

The hydrocolloid gellan gum, in particular, can advantageously be used as an admixture to the gelatin in a shell material mixture for the preparation of a capsule according to the invention. Gellan gum is a gel-forming polysaccharide that is prepared by fermentation with the aid of microorganisms.

U.S. Pat. No. 4,517,216 (Merck) already describes mixtures of gelatin and gellan gum. By means of a gellan gum content of 16% -83%, based on the sum of the gellan gum amount and gelatin amount, a high gel strength of the shell is achieved as a result of a synergistic effect. It is also described that only the deacylated and partially deacylated forms of gellan gum give rise to this effect, but not the native gellan gum.

JP 4027352 (Fuji) describes soft gelatin capsules, which are prepared by the rotary die process and which dissolve only in the intestinal tract. Here the change in the solubility of the shell is caused by the addition of hydrocolloids which form a gel with calcium ions, such as, for example, gellan gum. The disadvantage with this procedure is the addition of calcium ions to the shell solution. Preparation of seamless capsules by the multi-component nozzle method is not possible with this shell mixture since the viscosity and the gel point of the shell solution are too high as a result of the calcium ions.

JP 1037259 (San Ei) describes gelatin capsules having a gellan gum content in the shell to achieve an improved shell strength. In these capsules the shell contains 0.08% -2.4% gellan gum based on the sum of the gellan gum amount and gelatin amount. The solids content of the shell is at least 50%. Because of the high viscosity caused as a result, this formulation is not suitable for a multi-component nozzle process for the preparation of seamless capsules.

JP 63170310 (San Ei) describes capsules with shells consisting of gellan gum and other hydrocolloids, including gelatin. With these capsules the proportion of gellan gum in the total mass of the hydrocolloids is in the range 50-80% (m/m). The aim is to achieve as high as possible a gelling temperature and gelling rate.

U.S. No. 2001/0024678 A1 describes gelatin compositions for two-part capsules, where gellan gum can be used as a constituent of a setting system. The two-pan capsules described in the examples we hard capsules with a dissolving power that would not be acceptable for the purposes of the present invention.

A disadvantage of the embodiments given above is that they are not tailored to the method for the preparation of seamless soft gelatin capsules by the multi-component nozzle method. If the multi-component nozzle method with immersed nozzle is to be used for the preparation of a capsule according to the invention, it is essential when using gellan gum in the shell material to make the correct choice of the gellan gum type and the gellan gum amount so that the shell does not solidify even before the capsule formation has been completed. Moreover, the viscosity of the shell solution must not be too high.

In order to achieve an increased temperature stability, gellan gum is advantageously added to the shell mixture for the preparation of a capsule according to the invention; as a result the softening temperature of the shell increases considerably and the gelling temperature of the mixture is also considerably increased. For the preparation of capsules according to the invention by the multi-component nozzle method with immersed nozzle, the gelling temperature should not be above 50° C. and the viscosity of the shell solution at 80° C. should not be above 300 mpas; otherwise capsule formation is made more difficult or is not achievable. Therefore, the gellan gum type and amount must be selected in a particularly targeted manner.

There are high-acylated and low-acylated gellan gum grades. A low-acylated gellan gum, preferably the KELCO-GEL F grade from Kelco, a division of Merck & Co, is preferably used for the preparation of capsules according to the invention. Hard, transparent gels can be obtained using low-acylated gellan gum grades.

The preparation of capsules according to the invention by the multi-component nozzle process is problematical with a high-acylated gellan gum grade, such as, for example, KELCOGEL LT100 from Kelco, since during capsule shaping the capsules do not release from the coaxial nozzle without disturbance because of high elasticity of the shell. Moreover, undesired turbid and very highly elastic soft gels are produced.

In a preferred aqueous shell mixture (shell solution) for the preparation of a capsule according to the invention gelatin, with a content of >15% (m/m), based on the total mass of the shell solution, makes up the major proportion of hydrocolloids used in the total mass. In addition, gellan gum is used in a proportion of at most 0.6% (m/m), preferably a proportion in the range between 0.2 and 0.5% (m/m).

Higher proportions of gellan gum substantially increase the viscosity of the shell solution during capsule shaping and substantially reduce the solubility of the dried capsule shell in the mouth, which is not desired.

Lower proportions of gellan gum have no particular effect with regard to improved temperature stability of the dried capsule.

The presence of gellan gum leads to the formation of a solid network in the shell of a capsule according to the invention, which solid network as a rule does not dissolve in the moist state, even at 40-60° C. This network should make up only a relatively small proportion of the shell as a strengthening element. The fractions of non-crosslinked gelatin and further additives such as, for example, plasticizers, should, on the other hand, dissolve particularly rapidly in the mouth.

Capsules according to the invention that contain gellan gum in a range of 0.4-3% (m/m), preferably of 0.8-2% (m/m), based on the solids content of the shell are preferred. A preferred mass ratio of gellan gum to gelatin in the range of 1:23 to 1:230, preferably of 1:35 to 1:115 is obtained with gelatin contents of 70-90% (m/m), based on the solids content of the shell.

The gelatin fraction in these capsules can, in particular, also contain fractions of 0-Bloom gelatin and/or low-Bloom fish gelatin (in this context see above).

Core Liquid:

When a capsule according to the invention is prepared by the multi-component nozzle method the core liquid is hydrophobic and able to form a two-phase system with aqueous solutions.

On consumption of the large capsules according to the invention (capsule diameter in the range of 4-8 mm, thickness of the shell in the range of 20-200 µm) a relatively large amount of liquid passes directly into the mouth. This should give rise to an immediate flavor impression that is as strong as possible.

Therefore, mixtures of flavorings with vegetable oils or triglycerides are preferably used for the core liquid. The mixture is preferably a clear solution at room temperature and preferably also still a clear solution 10° C. Examples of suitable flavorings are synthetic and natural flavorings and mixtures thereof as well as also oleoresins or extracts of plants, leaves, flowers, fruit and the like, as well as combinations thereof. Flavorings from the series comprising peppermint oil, spearmint oil, eucalyptus oil, cinnamon oil, cassia oil, aniseed oil, bitter almond oil, oil of cloves, citrus oils, fruity flavoring compositions having tastes oriented towards, for example, apple, pear, peach, grape, strawberry, raspberry, cherry or pineapple, and individual components such as menthol, menthone and menthyl acetate are preferably used.

Flavoring Content in the Liquid Core:

The flavoring content in the core liquid depends, in particular, on the capsule size and the flavoring intensity and according to the invention ranges from 1-100%, based on the total mass of the liquid core. However, a flavoring content in the liquid core in the range of 5-90% (m/m), preferably 30-80% (m/m), based on the total mass of the liquid core, is preferred.

Sweeteners in the Liquid Core (Optional):

Sweeteners can also be added to the core liquid of a capsule according to the invention, with the use of solubilizing agents if appropriate. Since, in accordance with the intention, the core liquid comes into direct contact with the teeth in the mouth, it is advantageous if the core liquid does not exert a pH-lowering action. Otherwise it would not be possible to preclude damage to the enamel.

In the Applicant's research it has now been found that thaumatin, neohesperidine and miraculin (as well as mixtures thereof are particularly suitable as sweeteners in the core liquid and do not have an adverse effect on the pH value. On solubility grounds thaumatin is particularly preferred.

It has also been found that, on the other hand, other sweeteners that in principle are suitable for use, such as, for example, saccharinic acid or acesulfame K lower the pH value of the aqueous phase and therefore should not be used in relatively high concentrations if the change in the pH in the mouth is to remain tolerable.

To determine the effect on the pH, 20 ml aqueous phase were brought into contact with 5 ml of the core liquid containing sweeteners for 5 minutes at 25° C., with stirring. After phase separation, the pH value of the aqueous phase was determined. When saccharinic acid or acesulfame K was used the pH of the aqueous phase was reduced to below 4.

Oils in the Liquid Core:

Suitable oils for diluting the flavorings used are, in particular fractionated coconut oils which contain mainly C6-C8 fatty acid radicals. These oils are characterized by their neutral taste and by their good stability to oxidation.

Further Constituents of the Liquid Core (Optional):

Coloring substances, vitamins and/or vegetable extracts can be added to the core liquid.

Further, In Particular Physical, Capsule Properties:

Hardness:

Capsules according to the invention preferably have a hardness of 1000-4000 g. Capsules which, for example, have a hardness of 1500-3500 g for a diameter of 5 mm are preferred.

Harder capsules usually give rise to an unpleasant sensation in the mouth; softer capsules give rise to difficulties during transport since they are not mechanically stable.

In this context the hardness of the capsules is determined using a texture analyzer, for example using a TA-XT2i from Stable Micro Systems. With this method a stamp having a diameter of 2 mm is lowered at a constant forward speed of 0.5 mm/sec onto a capsule until the shell of this capsule breaks. The hardness of the capsule is designated as the weight in g that bears on the capsule at the break point.

See the examples for the hardness of capsules according to the invention.

Dissolving Power:

The shell of preferred capsules according to the invention dissolves in the in the (sic) mouth in less than 60 seconds, preferably in less than 45 seconds. The rate of dissolution can be determined by sensory means, the mechanical effects on moving the capsule in the mouth also being taken into account.

See the examples for the dissolving power of capsules according to the invention.

Appearance:

Capsules according to the invention are ball-shaped (spherical). Capsules according to the invention can be prepared by the multi-component nozzle method. The ratio between the largest and the smallest diameter of a spherical capsule according to the invention is not more than 1.2, preferably not more than 1.1. With a higher ratio the shell thickness becomes non-uniform and the capsule mechanically labile.

The shell of a capsule according to the invention is preferably transparent and glossy; therefore, separating agents should not be used during drying or packing after drying. In order to achieve a transparent shell, no additives to the shell mixture that cause the shell to become turbid should be used, even if the additives possess beneficial other properties and, for example, would have a beneficial effect on the solubility of the shell in the mouth, such as, for example, celluloses.

EXAMPLES

Preferred embodiments of the invention are explained in more detail below on the basis of examples.

Examples 1-29

Method for the Preparation of Capsules According to the Invention—General Procedure (Multi-Component Nozzle Method with Immersed Nozzle)

The constituents indicated in the appended table "Examples 1-29" for the shell mixture are added together and heated to 80° C. in a water bath until a clear solution that is essentially free from air bubbles has formed. Preferably solutions with solid contents of 20-40% (m/m) are used.

The core liquid is prepared at 10-20° C.

Shell liquid and core liquid are fed via a pump system to a concentric two-component nozzle. The line for the shell liquid is kept at 60-80° C. during this operation. The concentric two-component nozzle dips into a liquid bath that is filled with vegetable oil. The temperature of this oil bath is approximately 14° C.

With support from additional vibrational stimulus of the liquid, the liquid jet issuing from the nozzle into the oil bath disintegrates into individual droplets which are seamless capsules consisting of core and shell.

Adhering oil is removed from the capsules by centrifuging while the capsules are still wet and the capsules are then dried with continuous motion in a dry stream of air. Conventional vortex dryers or drum dryers can be used. The prerequisite for a good drying result is that the capsules can be kept in motion by rotation or by turbulent air. In some cases it is advisable to use an anti-blocking agent for this purpose.

However, in most cases the use of an anti-blocking agent is not desired. Specifically, a transparent and glossy shell is obtained if the composition of the shell mixture is so chosen that it is possible to dispense with the use of an anti-blocking agent such as, for example, silica during drying and there is nevertheless no sticking of the capsules.

Examples 1-29

TABLE 1

Composition and consumption characteristics of the dried capsules

Optimization of the plasticizer type/plasticizer amount/shell content

| No. | Capsule diameter [mm] | Shell-thickness [μm] | Shell thickness/capsule diameter ratio | Shell content [% (m/m)] | Core content [% (m/m)] | Composition of shell | Composition of core | Hardness [g] | Dissolution in the mouth [sec] |
|---|---|---|---|---|---|---|---|---|---|
| 1 | 5 | 140 | 0.028 | 15 | 85 | 80% pig gelatin 260 Bloom<br>10% glycerol<br>10% water* | 20% strawberry flavoring<br>80% vegetable oil | >6000 | 90 sec |
| 2 | 5 | 88 | 0.018 | 12 | 88 | 80% pig gelatin 260 Bloom<br>10% glycerol<br>10% water*<br>0.04% thaumatin | 30% peppermint flavoring<br>70% vegetable oil | 4860 | 55 sec |
| 3 | 5 | 80 | 0.016 | 10 | 90 | 80% pig gelatin 260 Bloom<br>10% glycerol<br>10% water* | 30% peppermint flavoring<br>70% vegetable oil | 4570 | 55 sec |
| 4 | 5 | 70 | 0.014 | 7.5 | 92.5 | 80% pig gelatin 260 Bloom<br>10% glycerol<br>10% water* | 20% strawberry flavoring<br>80% vegetable oil | 3290 | 50 sec |
| 5 | 5 | 50 | 0.010 | 7.5 | 92.5 | 80% pig gelatin 260 Bloom<br>10% glycerol<br>10% water* | 30% peppermint flavoring<br>70% vegetable oil | 3380 | 25 sec |
| 6 | 5 | 70 | 0.014 | 7.5 | 92.5 | 70% pig gelatin 260 Bloom<br>20% glycerol<br>10% water* | 15% peppermint flavoring<br>85% vegetable oil | 2160 | 45 sec |
| 7 | 5 | 55 | 0.011 | 7.5 | 92.5 | 70% pig gelatin 260 Bloom<br>20% glycerol<br>10% water* | 15% peppermint flavoring<br>85% vegetable oil | 1820 | 15 sec |
| 8 | 5 | 64 | 0.013 | 9 | 91 | 70% pig gelatin 260 Bloom<br>20% glycerol<br>10% water*<br>0.5% aspartame<br>0.5% acesulfame K<br>0.1% brilliant blue | 40% peppermint flavoring<br>60% vegetable oil | 1880 | 40 sec |
| 9 | 5 | 73 | 0.015 | 12 | 88 | 70% pig gelatin 260 Bloom<br>20% glycerol<br>10% water*<br>2.0% sucralose<br>0.1% brilliant blue | 65% mint flavoring<br>35% vegetable oil | 2670 | 40 sec |
| 10 | 6 | 77 | 0.013 | 7.5 | 92.5 | 70% pig gelatin 260 Bloom<br>20% glycerol<br>10% water*<br>0.05% aspartame<br>0.05% acesulfame K | 10% peppermint flavoring<br>90% vegetable oil | 1970 | 35 sec |
| 11 | 4 | 50 | 0.013 | 9 | 91 | 70% pig gelatin 260 Bloom<br>20% glycerol<br>10% water*<br>0.4% acesulfame K<br>0.1% brilliant blue | 30% peppermint flavoring<br>70% vegetable oil | 1460 | 10 sec |
| 12 | 5 | 122 | 0.024 | 15 | 85 | 70% pig gelatin 260 Bloom<br>20% glycerol<br>10% water* | 15% peppermint flavoring<br>85% vegetable oil | >6000 | 80 sec |
| 13 | 6 | 125 | 0.021 | 15 | 85 | 70% pig gelatin 260 Bloom<br>20% glycerol<br>10% water* | 10% peppermint flavoring<br>90% vegetable oil | >6000 | 60 sec |
| 14 | 7 | 150 | 0.021 | 15 | 85 | 70% pig gelatin 260 Bloom<br>20% glycerol<br>10% water* | 10% peppermint flavoring<br>90% vegetable oil | >6000 | 60 sec |
| 15 | 8 | 150 | 0.019 | 10 | 90 | 70% pig gelatin 260 Bloom<br>20% glycerol<br>10% water* | 10% peppermint flavoring<br>90% vegetable oil | >6000 | 60 sec |
| 16 | 5 | 64 | 0.013 | 8 | 92 | 70% pig gelatin 260 Bloom<br>20% glycerol<br>10% water*<br>0.05% aspartame<br>0.05% acesulfame K | 15% peppermint flavoring<br>85% vegetable oil | 2180 | 30 sec |
| 17 | 5 | 65 | 0.013 | 7.5 | 92.5 | 70% pig gelatin 260 Bloom<br>20% propylene glycol<br>10% water* | 15% peppermint flavoring<br>85% vegetable oil | 1550 | 30 sec |
| 18 | 5 | 55 | 0.01 | 7.5 | 92.5 | 60% pig gelatin 260 Bloom<br>30% propylene glycol<br>10% water* | 15% peppermint flavoring<br>85% vegetable oil | 900 | 25 sec |

TABLE 1-continued

Composition and consumption characteristics of the dried capsules

| No. | Capsule diameter [mm] | Shell-thickness [μm] | Shell thickness/ capsule diameter ratio | Shell content [% (m/m)] | Core content [% (m/m)] | Composition of shell | Composition of core | Hardness [g] | Dissolution in the mouth [sec] |
| --- | --- | --- | --- | --- | --- | --- | --- | --- | --- |
| 19 | 5 | 72 | 0.014 | 9 | 91 | 80% pig gelatin 260 Bloom<br>10% Sorbitol<br>10% water* | 15% peppermint flavoring<br>85% vegetable oil | 4000 | 40 sec |
| | | | | | | Effect of hydrocolloids | | | |
| 20 | 5 | 68 | 0.014 | 9 | 91 | 69% pig gelatin 260 Bloom<br>20% propylene glycol<br>10% water*<br>1% gellan gum KELCOGEL F | 50% peppermint flavoring<br>50% vegetable oil | not determined | 60 sec |
| 21 | 5 | 75 | 0.015 | 12 | 88 | 69% pig gelatin 260 Bloom<br>20% glycerol<br>10% water*<br>0.8% gellan gum KELCOGEL F | 50% peppermint flavoring<br>50% vegetable oil | not determined | 75 sec |
| 22 | 5 | 70 | 0.014 | 9 | 91 | 67% pig gelatin 260 Bloom<br>10% glycerol<br>10% water*<br>2% gellan gum KELCOGEL F | 50% peppermint flavoring<br>50% vegetable oil | not determined | 50 sec |
| | | | | | | Gelatin types | | | |
| 23 | 5 | 73 | 0.015 | 11 | 89 | 70% pig gelatin 260 Bloom<br>20% glycerol<br>10% water*<br>2.0% sucralose<br>0.1% brilliant blue | 65% mint flavoring<br>35% vegetable oil | 2670 | 40 sec |
| 24 | 5 | 60 | 0.012 | 7.5 | 92.5 | 70% cattle gelatin 240 Bloom<br>20% glycerol<br>10% water*<br>0.2% allura red | 30% cinnamon flavoring<br>70% vegetable oil | 2150 | 45 sec |
| 25 | 5 | 66 | 0.013 | 11 | 89 | 70% chicken gelatin 250 Bloom<br>20% glycerol<br>10% water*<br>2.0% sucralose<br>0.1% brilliant blue | 65% mint flavoring<br>35% vegetable oil | 3800 | 35 sec |
| 26 | 5 | 94 | 0.019 | 11 | 89 | 55% pig gelatin 260 Bloom<br>17% fish gelatin 0 Bloom<br>18% glycerol<br>10% water* | 65% mint flavoring<br>35% vegetable oil | 3240 | 25 sec |
| 27 | 5 | 80 | 0.016 | 11 | 89 | 55% chicken gelatin 260 Bloom<br>17% fish gelatin 0 Bloom<br>18% glycerol<br>10% water* | 65% mint flavoring<br>35% vegetable oil | 3520 | 30 sec |
| 28 | 5 | 75 | 0.015 | 11 | 89 | 35% chicken gelatin 250 Bloom<br>35% fish gelatin 110 Bloom<br>20% glycerol<br>10% water* | 65% mint flavoring<br>35% vegetable oil | 3000 | 25 sec |
| 29 | 5 | 72 | 0.014 | 11 | 89 | 70% fish gelatin 165 Bloom<br>20% glycerol<br>10% water*<br>2% gellan gum KELCOGEL F<br>2.0% sucralose<br>0.1% brilliant blue | 65% mint flavoring<br>35% vegetable oil | 2500 | 30 sec |

*Note: Adhering residual water depends on the atmospheric humidity and can therefore vary.
Gellan gum can be obtained from Kelco, a Division of Merck & Co. under the trade name KELCOGEL F
In the case of formulations containing gellan gum the shell mixture should be heated at 80° C. until a clear solution has formed. Cooling of the liquid surface should be avoided

TABLE 2

| | Composition of the aqueous shell solution | Gel point | Viscosity at 80° C. | Remarks | Flexibility* |
|---|---|---|---|---|---|
| A | 75% water<br>20% pig gelatin 260 Bloom<br>5% glycerol | 29° C. | 54 mPas | | low |
| B | 75% water<br>20% cattle gelatin 240 Bloom<br>5% glycerol | 34° C. | 61 mPas | | low |
| C | 75% water<br>20% chicken gelatin 250 Bloom<br>5% glycerol | 35° C. | 71 mPas | | low |
| D | 75% water<br>10% pig gelatin 260 Bloom<br>10% fish gelatin 110 Bloom<br>5% glycerol | 30° C. | 130 mPas | | moderate |
| E | 75% water<br>15% pig gelatin 260 Bloom<br>5% fish gelatin 0 Bloom<br>5% glycerol | 29° C. | 90 mPas | | high |
| F | 75% water<br>15% chicken gelatin 250 Bloom<br>5% fish gelatin 0 Bloom<br>5% glycerol | 32° C. | 85 mPas | | high |
| G | 75% water<br>19.6% fish gelatin 165 Bloom<br>0.4% gellan gum Kelcogel F<br>5% glycerol | 50° C. | 300 mPas | | low |
| H | 75% water<br>20% fish gelatin 110 Bloom<br>5% glycerol | 20° C. | 42 mPas | moist capsule shell too unstable for further process steps | moderate |
| I | 75% water<br>20% fish gelatin 165 Bloom<br>5% glycerol | 24° C. | 72 mPas | moist capsule shell too unstable for further process steps | moderate |
| K | 75% water<br>20% pig gelatin 80 Bloom<br>5% glycerol | 33° C. | 90 mPas | | low |

*Flexibility: Assessment on bending over a 200 μm thick film which had been produced from the shell solution by pouring out and drying in air (20° C., 40% relative atmospheric humidity, at least 20 h).

What is claimed is:

1. A spherical capsule comprising a liquid core and a seamless solid shell surrounding said core, wherein
   the capsule has a diameter in the range of 4-8 mm,
   the shell has a thickness in the range of 20-200 μm,
   the shell thickness to capsule diameter ratio is in the range of 0.004-0.04,
   the shell comprises 70-90% (m/m) gelatin and 10-30% (m/m) plasticizer, based on the solids content of the shell, and
   the core has a flavoring content in the range of 1-100% (m/m), based on the total mass of the core, wherein the shell comprises (a) a gelatin having a Bloom value of at least 200 and (b) a gelatin having a Bloom value of 0, a fish gelatin having a Bloom value of <200, or both.

2. The capsule according to claim 1, wherein
   the diameter of the capsule is in the range of 4.5-6.5 mm,
   the thickness of the shell is in the range of 50-150 μm,
   the shell thickness to capsule diameter ratio is in the range of 0.01-0.03.

3. The capsule according to claim 1, wherein the shell is prepared from a mixture containing gelatin and plasticizer which has a gel point in the range between 15° C. and 60° C.

4. The capsule according to claim 1, wherein the fish gelatin is a cold water fish gelatin and/or has a gel point of <20° C.

5. The capsule according to claim 1, wherein the liquid core contains a sweetener that is selected from the group that consists of thaumatin, neohesperidine, miraculin and mixtures thereof.

6. The capsule according to claim 1, wherein the concentration of the plasticizer in the shell is 10-30% (m/m), based on the total solids content of the shell.

7. The capsule according to claim 1, wherein the plasticizer comprises one or more polyols.

8. The capsule according to claim 1, wherein the gelatin is selected from the group that consists of pig gelatin, cattle gelatin, chicken gelatin, fish gelatin and mixtures thereof.

9. The capsule according to claim 1 wherein the shell contains a sweetener that is selected from the group that consists of sucralose, aspartame, acesulfame K, thaumatin, Na saccharine, neohesperidin and mixtures thereof.

10. The capsule according to claim 1, wherein the shell contains gellan gum.

11. The capsule according to claim 10, wherein the shell contains 0.4-3% (m/m) gellan gum, based on the solids content of the shell.

12. The capsule according to claim 2, wherein
the diameter of the capsule is in the range of 4.5-5.5 mm,
the thickness of the shell is in the range of 50-90 μm, and
the shell thickness to capsule diameter ratio is in the range of 0.01-0.02.

13. The capsule according to claim 3, wherein the shell is prepared from a mixture containing gelatin and plasticizer which has a gel point in the range between 20° C. and 40° C.

14. The capsule according to claim 13, wherein the shell is prepared from a mixture containing gelatin and plasticizer which has a gel point in the range between 25° C. and 35° C.

15. The capsule according to claim 1, wherein a gelatin having a Bloom value in the range of 240-300 is used for the preparation of the shell.

16. The capsule according to claim 6, wherein the concentration of the plasticizer in the shell is 15-20% (m/m), based on the total solids content of the shell.

17. The capsule according to claim 7, wherein said polyol is selected from the group that consists of glycerol, propylene glycol, sorbitol and maltitol.

18. A method for the preparation of a capsule according to claim 1, said method comprising simultaneously pumping a liquid core material and a gelatin-containing curable shell mixture through a concentric multi-component nozzle so that they drip into a cooling liquid with the formation of a capsule.

19. The method according to claim 18, wherein said curable shell mixture comprises gelatin and plasticizer.

20. The method of claim 18, further comprising the step of adjusting the hardness and dissolving power of the shell of said spherical capsule using a mixture consisting of (a) a gelatin having a Bloom value of at least 200 and (b) a gelatin having a Bloom value of 0 and/or a fish gelatin.

21. A spherical capsule comprising a liquid care and a seamless solid shell surrounding said core, wherein
the capsule has a diameter in the range of 4-8 mm,
the shell has a thickness in the range of 20-200 μn,
the shell thickness to capsule diameter ratio is in the range of 0.004-0.04,
the shell comprises 70-90% (m/m) gelatin and 10-30% (m/m) plasticizer, based on the solids content of the shell, and
the core has a flavoring content in the range of 1-100% (m/m), based on the total mass of the core, wherein the shell contains gellan gum.

22. A spherical capsule comprising a liquid core and a seamless solid shell surrounding said cores, wherein
the capsule has a diameter in the range of 4-8 mm,
the shell has a thickness in the range of 20-200 μm,
the shell thickness to capsule diameter ratio is in the range of 0.004-0.04,
the shell comprises 70-90% (m/m) gelatin and 10-30% (m/m) plasticizer, based on the solids content of the shell, and
the core has a flavoring content in the range of 1-100% (m/m), based on the total mass of the core, wherein the shell contains 0.4-3% (m/m) gellan gum, based on the solids content of the shell.

* * * * *